US006204022B1

(12) United States Patent
Johnson et al.

(10) Patent No.: US 6,204,022 B1
(45) **Date of Patent: *Mar. 20, 2001**

(54) LOW-TOXICITY HUMAN INTERFERON-ALPHA ANALOGS

(75) Inventors: Howard M. Johnson, Gainesville, FL (US); Carol H. Pontzer, Silver Springs, MD (US); Prem S. Subramaniam, Gainesville, FL (US); Lorelie H. Villarete, Alameda; Jackeline Campos, Pittsburg, both of CA (US)

(73) Assignee: Pepgen Corporation and University of Florida

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/954,395

(22) Filed: Oct. 20, 1997

Related U.S. Application Data

(63) Continuation-in-part of application No. 08/631,328, filed on Apr. 12, 1996, now Pat. No. 5,939,286.

(51) Int. Cl.[7] .......................... C12N 15/21; C07K 14/56; C07K 14/555; A61K 38/21

(52) U.S. Cl. .................................. 435/69.51; 536/23.52; 530/351; 424/85.4; 424/85.7

(58) Field of Search .......................... 530/351; 424/85.4, 424/85.7; 435/69.51; 536/23.52

(56) References Cited

U.S. PATENT DOCUMENTS

| | | | |
|---|---|---|---|
| 4,276,282 | 6/1981 | Sugimoto et al. . | |
| 4,414,150 | 11/1983 | Goeddel . | |
| 4,456,748 | 6/1984 | Goeddel . | |
| 4,460,574 | 7/1984 | Yabrov . | |
| 4,507,281 | 3/1985 | Asculai et al. . | |
| 4,569,908 | 2/1986 | Mark et al. . | |
| 4,636,383 | 1/1987 | Nagabhushan et al. . | |
| 4,758,428 | 7/1988 | Mark et al. . | |
| 4,846,782 | 7/1989 | Bonnem . | |
| 4,874,609 | 10/1989 | Rideout et al. . | |
| 4,892,743 | 1/1990 | Leibowitz et al. . | |
| 4,897,471 | 1/1990 | Stabinsky . | |
| 4,917,887 | 4/1990 | Hauptmann et al. . | |
| 5,019,382 | 5/1991 | Cummins . | |
| 5,705,363 | 1/1998 | Imakawa et al. . | |
| 5,939,286 * | 8/1999 | Johnson et al. | 435/69.51 |

FOREIGN PATENT DOCUMENTS

| | | |
|---|---|---|
| 0 146 903 A2 | 7/1985 | (EP) . |
| 240 224 A2 | 10/1987 | (EP) . |
| WO 83/02461 | 7/1983 | (WO) . |
| WO 94/10313 | 5/1994 | (WO) . |

OTHER PUBLICATIONS

Bazer, F.W., et al., "Role of Conceptus Secretory Products in Establishment of Pregnancy," *J. Reprod. Fert.* 76:841–850 (1986).

Bonnem, E.M., and Spiegel, R.J., "Interferon–α: Current Status and Future Promise," *J. Biological Response Modifiers* 3:580–598 (1984).

Godkin, et al., "Proteins Release by Cultured Day 15–16 Conceptuses Prolong Luteal Maintenance When Introduced into the Uterine Lumen of Cyclic Ewes," *J. Reprod. Fertil.* 71:57–64 (1984).

Imakawa, K., et al., "Interferon–Like Sequence of Ovine Trophoblast Protein Secreted by Embryonic Trophectoderm," *Nature* 330:377–379 (1987).

Jarpe, M.A., et al., "Predicted Structural Motif of IFNΓ," *Prot. Engin.* 7(7):863–867 (1994).

Li, J., and Roberts, R.M., "Structure–Function Relationships in the Interferon–Γ(IFN–Γ): Changes in Receptor Binding and in Antiviral and Antiproliferative Activities Resulting from Site–Directed Mutagenesis Performed Near the Carboxyl Terminus," *J. Biol. Chem.* 269(40):24826–24833 (1994).

Oldham, R.K., "Biologicals for Cancer Treatment: Interferons," *Hosp. Pract.* Dec. 15, pp. 71–86 (1985).

Ott, T.L., et al., "Cloning and Expression in *Saccharomyces cerevisiae* of a Synthetic Gene for the Type–I Trophoblast Interferon Ovine Trophoblast Protein–1: Purification and Antiviral Activity," *J. Interferon Res.* 11:357–364 (1991).

Pontzer, C.J., et al., "Antiviral Activity of the Pregnancy Recognition Hormone Ovine Trophoblast Protein–1," *Biochem. Biophys. Res. Comm.* 152:801–807 (1988).

Pontzer, C.J., et al., "Structure/Function Studies with Interferon Tau: Evidence for Multiple Active Sites," *J. Interferon Res.* 14:133–141 (1994).

Quesada, J.R., et al., "Alpha Interferon for Induction of Remission in Hairy–Cell Leukemia," *N. Engl. J. Med.* 310:15–18 (1984).

Salamonsen, L.A., et al., "Interferon–Alpha Mimics Effects of Ovine Trophoblast Protein 1 on Prostaglandin and Protein Secretion by Ovine Endometrial Cells In Vitro," *J. Endocrin.* 117:R1–R4 (1988).

Soos, J.M., et al., "The IFN Pregnancy Recognition Hormone IFN–ΓBlocks Both Development and Superantigen Reactivation of Experimental Allergic Encephalomyelitis Without Associated Toxicity," *J. Immunol.* 155:2747–2753 (1995).

Stewart, H.J., et al., "Interferon Sequence Homology and Receptor Binding Activity of Ovine Trophoblast Antileuteolytic Protein," *J. Endicrinol.* 115:R13–R15 (1987).

(List continued on next page.)

*Primary Examiner*—David L. Fitzgerald
(74) *Attorney, Agent, or Firm*—Joanne Petithory; Judy M. Mohr; Iota Pi Law Group

(57) ABSTRACT

The invention describes a method of reducing the cytotoxicity of interferon-alpha by making defined amino acid substitutions in the N-terminal portion of the polypeptide sequence. Also described are human interferon-alpha analogs with low cytotoxicity, and therapeutic applications of the low toxicity interferon-alpha analogs.

42 Claims, 1 Drawing Sheet

OTHER PUBLICATIONS

Subramaniam, P.S., and Johnson, H.M., "Differential Recognition of the Type I Receptor by the Type I Interferons, IFNΓ and IFNα, is Responsible for Their Differential Cytotoxicites," *FASEB J.* 9(4):A1021 Abstract (1995).

Subramaniam, P.S., et al., "Differential Recognition of the Type I Interferon Receptor by Interferons Γ and α is Responsible for Their Disparate Cytotoxicities," *Proc. Natl. Acad. Sci. USA* 92:12270–12274 (1995).

Whaley, A.E., et al., "Identification and Cellular Localization of Unique Interferon mRNA from Human Placenta," *The Journal of Biological Chemistry* 269(14):10864–10868 (1994).

White, et al., in *Principles of Biochemistry*, McGraw–Hill, New York, NY, 6th Edition, pp. 860–874 (1978).

Wilson, M.E., et al., "Proteins of Ovine Blastocyst Origin," *Biol. Reproduct.* 20(Sup 1):101A Abstract (1979).

* cited by examiner 10 20 27

CDLPETHSLDNRRTLMLLAQMSRISPS -- rhIFN-α
CYLSRKLMLDARENLKLLDRMNRLSPH -- roIFN-τ

CYLSRKLMLDARENLKLLDRMNRLSPH -- IFNα-N0
CYLSRTHSLDNRRTLMLLAQMSRISPS -- IFNα-N1
CYLSRKLMLDNRRTLMLLAQMSRISPS -- IFNα-N2
CYLSRKLMLDARENLMLLAQMSRISPS -- IFNα-N3
CYLSRKLMLDARENLKLLDRMSRISPS -- IFNα-N4
CDLPEKLMLDARENLKLLDRMNRLSPH -- IFNα-N5
CDLPETHSLDARENLKLLDRMNRLSPH -- IFNα-N6
CDLPETHSLDNRRTLMLLDRMNRLSPH -- IFNα-N7

Fig. 1

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (v) FRAGMENT TYPE: internal (vii) IMMEDIATE SOURCE:
(B) CLONE: mature HuIFN-alpha residues 19-27

(xi) SEQUENCE DESCRIPTION: SEQ ID NO:1:

```
Ala Gln Met Ser Arg Ile Ser Pro Ser
 1               5
```

(2) INFORMATION FOR SEQ ID NO:2:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (v) FRAGMENT TYPE: internal (vii) IMMEDIATE SOURCE:
(B) CLONE: mature OvIFN-tau residues 19-27

(xi) SEQUENCE DESCRIPTION: SEQ ID NO:2:

```
Asp Arg Met Asn Arg Leu Ser Pro His
 1               5
```

(2) INFORMATION FOR SEQ ID NO:3:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (v) FRAGMENT TYPE: internal (vii) IMMEDIATE SOURCE:
(B) CLONE: mature HuIFN-alpha residues 11-27

(xi) SEQUENCE DESCRIPTION: SEQ ID NO:3:

```
Asn Arg Arg Thr Leu Met Leu Leu Ala Gln Met Ser Arg Ile Ser Pro
 1               5                  10                  15

Ser
```

(2) INFORMATION FOR SEQ ID NO:4:

(i) SEQUENCE CHARACTERISTICS:
(A) LENGTH: 17 amino acids
(B) TYPE: amino acid
(C) STRANDEDNESS: single -continued

```
        (D) TOPOLOGY: linear

    (ii) MOLECULE TYPE: peptide

     (v) FRAGMENT TYPE: internal

   (vii) IMMEDIATE SOURCE:
          (B) CLONE: mature OvIFN-tau residues 11-27

    (xi) SEQUENCE DESCRIPTION: SEQ ID NO:4:

Ala Arg Glu Asn Leu Lys Leu Leu Asp Arg Met Asn Arg Leu Ser Pro
 1               5                  10                  15

His


(2) INFORMATION FOR SEQ ID NO:5:

     (i) SEQUENCE CHARACTERISTICS:
          (A) LENGTH: 22 amino acids
          (B) TYPE: amino acid
          (C) STRANDEDNESS: single
          (D) TOPOLOGY: linear

    (ii) MOLECULE TYPE: peptide

     (v) FRAGMENT TYPE: internal

   (vii) IMMEDIATE SOURCE:
          (B) CLONE: mature HuIFN-alpha residues 6-27

    (xi) SEQUENCE DESCRIPTION: SEQ ID NO:5:

Thr His Ser Leu Asp Asn Arg Arg Thr Leu Met Leu Leu Ala Gln Met
 1               5                  10                  15

Ser Arg Ile Ser Pro Ser
            20


(2) INFORMATION FOR SEQ ID NO:6:

     (i) SEQUENCE CHARACTERISTICS:
          (A) LENGTH: 22 amino acids
          (B) TYPE: amino acid
          (C) STRANDEDNESS: single
          (D) TOPOLOGY: linear

    (ii) MOLECULE TYPE: peptide

     (v) FRAGMENT TYPE: internal

   (vii) IMMEDIATE SOURCE:
          (B) CLONE: mature OvIFN-tau residues 6-27

    (xi) SEQUENCE DESCRIPTION: SEQ ID NO:6:

Lys Leu Met Leu Asp Ala Arg Glu Asn Leu Lys Leu Leu Asp Arg Met
 1               5                  10                  15

Asn Arg Leu Ser Pro His
            20


(2) INFORMATION FOR SEQ ID NO:7:

     (i) SEQUENCE CHARACTERISTICS:
          (A) LENGTH: 27 amino acids
          (B) TYPE: amino acid
          (C) STRANDEDNESS: single
          (D) TOPOLOGY: linear

    (ii) MOLECULE TYPE: peptide

     (v) FRAGMENT TYPE: N-terminal

   (vii) IMMEDIATE SOURCE:
          (B) CLONE: mature HuIFN-alpha residues 1-27
```

-continued (xi) SEQUENCE DESCRIPTION: SEQ ID NO:7:

```
Cys Asp Leu Pro Glu Thr His Ser Leu Asp Asn Arg Arg Thr Leu Met
 1              5                  10                  15

Leu Leu Ala Gln Met Ser Arg Ile Ser Pro Ser
            20                  25
```

(2) INFORMATION FOR SEQ ID NO:8:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: peptide (v) FRAGMENT TYPE: N-terminal (vii) IMMEDIATE SOURCE:
(B) CLONE: mature OvIFN-tau residues 1-27

(xi) SEQUENCE DESCRIPTION: SEQ ID NO:8:

```
Cys Tyr Leu Ser Arg Lys Leu Met Leu Asp Ala Arg Glu Asn Leu Lys
 1              5                  10                  15

Leu Leu Asp Arg Met Asn Arg Leu Ser Pro His
            20                  25
```

(2) INFORMATION FOR SEQ ID NO:9:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(A) LIBRARY: GenBank Accessn. J00210, PID g386796
(B) CLONE: Human IFN alpha-d, mature protein (xi) SEQUENCE DESCRIPTION: SEQ ID NO:9:

```
Cys Asp Leu Pro Glu Thr His Ser Leu Asp Asn Arg Arg Thr Leu Met
 1              5                  10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160
```

```
Arg Leu Arg Arg Lys Glu
                165
```

(2) INFORMATION FOR SEQ ID NO:10:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N0

(xi) SEQUENCE DESCRIPTION: SEQ ID NO:10:

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:11:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N1

(xi) SEQUENCE DESCRIPTION: SEQ ID NO:11:

```
Cys Tyr Leu Ser Arg Thr His Ser Leu Asp Asn Arg Arg Thr Leu Met
 1               5                  10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
```

-continued

```
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:12:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N2

(xi) SEQUENCE DESCRIPTION: SEQ ID NO:12:

```
Cys Tyr Leu Ser Arg Lys Leu Met Leu Asp Asn Arg Arg Thr Leu Met
 1               5                  10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:13:

(i) SEQUENCE CHARACTERISTICS:
(A) LENGTH: 166 amino acids
(B) TYPE: amino acid
(C) STRANDEDNESS: single -continued

```
        (D) TOPOLOGY: linear

   (ii) MOLECULE TYPE: protein

  (vii) IMMEDIATE SOURCE:
        (B) CLONE: HuIFN-alpha analog IFNa-N3

   (xi) SEQUENCE DESCRIPTION: SEQ ID NO:13:

Cys Tyr Leu Ser Arg Lys Leu Met Leu Asp Ala Arg Glu Asn Leu Met
 1               5                  10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165


(2) INFORMATION FOR SEQ ID NO:14:

    (i) SEQUENCE CHARACTERISTICS:
        (A) LENGTH: 166 amino acids
        (B) TYPE: amino acid
        (C) STRANDEDNESS: single
        (D) TOPOLOGY: linear

   (ii) MOLECULE TYPE: protein

  (vii) IMMEDIATE SOURCE:
        (B) CLONE: HuIFN-alpha analog IFNa-N4

   (xi) SEQUENCE DESCRIPTION: SEQ ID NO:14:

Cys Tyr Leu Ser Arg Lys Leu Met Leu Asp Ala Arg Glu Asn Leu Lys
 1               5                  10                  15

Leu Leu Asp Arg Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110
```

-continued

```
Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:15:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N5

(xi) SEQUENCE DESCRIPTION: SEQ ID NO:15:

```
Cys Asp Leu Pro Glu Lys Leu Met Leu Asp Ala Arg Glu Asn Leu Lys
 1               5                  10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:16:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N6

(xi) SEQUENCE DESCRIPTION: SEQ ID NO:16:

```
Cys Asp Leu Pro Glu Thr His Ser Leu Asp Ala Arg Glu Asn Leu Lys
 1               5                  10                  15
```

-continued

```
Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:17:

(i) SEQUENCE CHARACTERISTICS:
(A) LENGTH: 166 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: HuIFN-alpha analog IFNa-N7

(xi) SEQUENCE DESCRIPTION: SEQ ID NO:17:

```
Cys Asp Leu Pro Glu Thr His Ser Leu Asp Asn Arg Arg Thr Leu Met
 1               5                  10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

(2) INFORMATION FOR SEQ ID NO:18:

(i) SEQUENCE CHARACTERISTICS:
(A) LENGTH: 172 amino acids
(B) TYPE: amino acid
(C) STRANDEDNESS: single
(D) TOPOLOGY: linear (ii) MOLECULE TYPE: protein (vii) IMMEDIATE SOURCE:
(A) LIBRARY: GenBank Accessn. Y00287, PID g1358
(B) CLONE: Ovine IFN-tau, mature protein (xi) SEQUENCE DESCRIPTION: SEQ ID NO:18:

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

(2) INFORMATION FOR SEQ ID NO:19:

(i) SEQUENCE CHARACTERISTICS:
(A) LENGTH: 527 base pairs
(B) TYPE: nucleic acid
(C) STRANDEDNESS: single
(D) TOPOLOGY: linear (vii) IMMEDIATE SOURCE:
(B) CLONE: IFNa-N0 synthetic gene (xi) SEQUENCE DESCRIPTION: SEQ ID NO:19:

```
CTAGGCTCGA GAAGAGATGT TACTTGTCTA GAAAGTTGAT GTTGGACGCC AGAGAGAACT     60

TGAAGTTGTT GGATAGAATG AACAGACTTT CTCCTCACTC TTGTCTTATG GACAGACACG    120

ACTTCGGTTT CCCACAAGAA GAATTTGACG GTAACCAATT CCAAAAGGCT CCAGCTATCT    180

CTGTCTTGCA CGAGTTGATC CAACAAATTT TCAACCTTTT CACTACCAAG GACTCCTCCG    240

CTGCTTGGGA CGAAGATTTG CTTGACAAGT TCTGTACTGA GCTTTACCAA CAATTGAACG    300

ACTTGGAAGC CTGTGTCATG CAAGAAGAGA GAGTTGGAGA GACCCCTTTG ATGAACGCTG    360

ATTCCATTTT GGCTGTCAAG AAGTACTTCA GAAGAATTAC CTTGTACCTT ACTGAGAAGA    420
```

-continued

```
AGTACTCTCC ATGTGCTTGG GAGGTTGTTA GAGCTGAAAT TATGAGATCC TTGTCTTTGT    480

CTACTAACCT TCAAGAAAGA TTGAGAAGAA AGGAGTAAGC GGCCGCG                  527


(2) INFORMATION FOR SEQ ID NO:20:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

   (vii) IMMEDIATE SOURCE:
          (B) CLONE: Linker 1

    (xi) SEQUENCE DESCRIPTION: SEQ ID NO:20:

CTAGAAAGTT GATGGAATTC GACG                                            24


(2) INFORMATION FOR SEQ ID NO:21:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

   (vii) IMMEDIATE SOURCE:
          (B) CLONE: Linker 2

    (xi) SEQUENCE DESCRIPTION: SEQ ID NO:21:

GTTACCGTCG AATTCCATCA ACTTT                                           25


(2) INFORMATION FOR SEQ ID NO:22:

     (i) SEQUENCE CHARACTERISTICS:
          (A) LENGTH: 135 base pairs
          (B) TYPE: nucleic acid
          (C) STRANDEDNESS: single
          (D) TOPOLOGY: linear

   (vii) IMMEDIATE SOURCE:
          (B) CLONE: Frag N1, forward strand

    (xi) SEQUENCE DESCRIPTION: SEQ ID NO:22:

TCGAGAAGAG ATGTTACCTT TCTAGAACCC ACTCCTTGGA CAACAGAAGA ACCTTGATGT     60

TGCTAGCCCA AATGTCCAGA ATCTCCCCTT CCTCTTGTCT TATGGACAGA CACGACTTCG    120

GTTTCCCACA AGAAG                                                     135


(2) INFORMATION FOR SEQ ID NO:23:

     (i) SEQUENCE CHARACTERISTICS:
          (A) LENGTH: 135 base pairs
          (B) TYPE: nucleic acid
          (C) STRANDEDNESS: single
          (D) TOPOLOGY: linear

   (vii) IMMEDIATE SOURCE:
          (B) CLONE: Frag N1, reverse strand

    (xi) SEQUENCE DESCRIPTION: SEQ ID NO:23:

AATTCTTCTT GTGGGAAACC GAAGTCGTGT CTGTCCATAA GACAAGAGGA AGGGGAGATT     60

CTGGACATTT GGGCTAGCAA CATCAAGGTT CTTCTGTTGT CCAAGGAGTG GGTTCTAGAA    120

AGGTAACATC TCTTC                                                     135


(2) INFORMATION FOR SEQ ID NO:24:
```

-continued (i) SEQUENCE CHARACTERISTICS:
(A) LENGTH: 100 base pairs
(B) TYPE: nucleic acid
(C) STRANDEDNESS: single
(D) TOPOLOGY: linear (vii) IMMEDIATE SOURCE:
(B) CLONE: Frag N2, forward strand (xi) SEQUENCE DESCRIPTION: SEQ ID NO:24:

TCGAGAAGAG ATGTTACTTG TCTAGAAAGT TGATGTTGGA CAACAGAAGA ACCCTTATGC 60

TGCTAGCTCA AATGTCCAGA ATCTCTCCAT CCTCTTGTCT 100

(2) INFORMATION FOR SEQ ID NO:25:

(i) SEQUENCE CHARACTERISTICS:
(A) LENGTH: 116 base pairs
(B) TYPE: nucleic acid
(C) STRANDEDNESS: single
(D) TOPOLOGY: linear (vii) IMMEDIATE SOURCE:
(B) CLONE: Frag N2, reverse strand (xi) SEQUENCE DESCRIPTION: SEQ ID NO:25:

CGAAGTCGTG TCTGTCCATA AGACAAGAGG ATGGAGAGAT TCTGGACATT TGAGCTAGCA 60

GCATAAGGGT TCTTCTGTTG TCCAACATCA ACTTTCTAGA CAAGTAACAT CTCTTC 116

(2) INFORMATION FOR SEQ ID NO:26:

(i) SEQUENCE CHARACTERISTICS:
(A) LENGTH: 100 base pairs
(B) TYPE: nucleic acid
(C) STRANDEDNESS: single
(D) TOPOLOGY: linear (vii) IMMEDIATE SOURCE:
(B) CLONE: Frag N3, forward strand (xi) SEQUENCE DESCRIPTION: SEQ ID NO:26:

TCGAGAAGAG ATGTTACTTG TCTAGAAAGT TGATGTTGGA CGCTAGAGAG AACTTGATGC 60

TGCTAGCTCA AATGTCCAGA ATTTCCCCTT CTTCTTGTCT 100

(2) INFORMATION FOR SEQ ID NO:27:

(i) SEQUENCE CHARACTERISTICS:
(A) LENGTH: 116 base pairs
(B) TYPE: nucleic acid
(C) STRANDEDNESS: single
(D) TOPOLOGY: linear (vii) IMMEDIATE SOURCE:
(B) CLONE: Frag N3, reverse strand (xi) SEQUENCE DESCRIPTION: SEQ ID NO:27:

CGAAGTCGTG TCTGTCCATA AGACAAGAAG AAGGGGAAAT TCTGGACATT TGAGCTAGCA 60

GCATCAAGTT CTCTCTAGCG TCCAACATCA ACTTTCTAGA CAAGTAACAT CTCTTC 116

(2) INFORMATION FOR SEQ ID NO:28:

(i) SEQUENCE CHARACTERISTICS:
(A) LENGTH: 100 base pairs
(B) TYPE: nucleic acid
(C) STRANDEDNESS: single
(D) TOPOLOGY: linear (vii) IMMEDIATE SOURCE:

-continued (B) CLONE: Frag N4, forward strand (xi) SEQUENCE DESCRIPTION: SEQ ID NO:28:

TCGAGAAGAG ATGTTACTTG TCTAGAAAGT TGATGCTTGA CGCTAGAGAA AACTTGAAGC 60

TTTTGGACAG AATGTCCAGA ATTTCCCCAT CCTCTTGTCT 100

(2) INFORMATION FOR SEQ ID NO:29:

(i) SEQUENCE CHARACTERISTICS:
(A) LENGTH: 116 base pairs
(B) TYPE: nucleic acid
(C) STRANDEDNESS: single
(D) TOPOLOGY: linear (xi) SEQUENCE DESCRIPTION: SEQ ID NO:29:

CGAAGTCGTG TCTGTCCATA AGACAAGAGG ATGGGGAAAT TCTGGACATT CTGTCCAAAA 60

GCTTCAAGTT TTCTCTAGCG TCAAGCATCA ACTTTCTAGA CAAGTAACAT CTCTTC 116

(2) INFORMATION FOR SEQ ID NO:30:

(i) SEQUENCE CHARACTERISTICS:
(A) LENGTH: 135 base pairs
(B) TYPE: nucleic acid
(C) STRANDEDNESS: single
(D) TOPOLOGY: linear (vii) IMMEDIATE SOURCE:
(B) CLONE: Frag N5, forward strand (xi) SEQUENCE DESCRIPTION: SEQ ID NO:30:

TCGAGAAGAG ATGTGACTTG CCAGAAAAGC TTATGTTGGA CGCCAGAGAA AACTTGAAAC 60

TTCTAGACAG AATGAACAGA TTGTCTCCAC ACTCTTGTCT TATGGACAGA CACGACTTCG 120

GTTTCCCACA AGAAG 135

(2) INFORMATION FOR SEQ ID NO:31:

(i) SEQUENCE CHARACTERISTICS:
(A) LENGTH: 135 base pairs
(B) TYPE: nucleic acid
(C) STRANDEDNESS: single
(D) TOPOLOGY: linear (vii) IMMEDIATE SOURCE:
(B) CLONE: Frag N5, reverse strand (xi) SEQUENCE DESCRIPTION: SEQ ID NO:31:

AATTCTTCTT GTGGGAAACC GAAGTCGTGT CTGTCCATAA GACAAGAGTG TGGAGACAAT 60

CTGTTCATTC TGTCTAGAAG TTTCAAGTTT TCTCTGGCGT CCAACATAAG CTTTTCTGGC 120

AAGTCACATC TCTTC 135

(2) INFORMATION FOR SEQ ID NO:32:

(i) SEQUENCE CHARACTERISTICS:
(A) LENGTH: 100 base pairs
(B) TYPE: nucleic acid
(C) STRANDEDNESS: single
(D) TOPOLOGY: linear (vii) IMMEDIATE SOURCE:
(B) CLONE: Frag N6, forward strand (xi) SEQUENCE DESCRIPTION: SEQ ID NO:32:

TCGAGAAGAG ATGTGACTTG CCTGAAACTC ACAGTCTAGA CGCCAGAGAG AACTTGAAGC 60

-continued

```
TTTTGGACAG AATGAACAGA TTGTCTCCAC ACTCTTGTCT                        100


(2) INFORMATION FOR SEQ ID NO:33:

     (i) SEQUENCE CHARACTERISTICS:
          (A) LENGTH: 116 base pairs
          (B) TYPE: nucleic acid
          (C) STRANDEDNESS: single
          (D) TOPOLOGY: linear

   (vii) IMMEDIATE SOURCE:
          (B) CLONE: Frag N6, reverse strand

    (xi) SEQUENCE DESCRIPTION: SEQ ID NO:33:

CGAAGTCGTG TCTGTCCATA AGACAAGAGT GTGGAGACAA TCTGTTCATT CTGTCCAAAA     60

GCTTCAAGTT CTCTCTGGCG TCTAGACTGT GAGTTTCAGG CAAGTCACAT CTCTTC        116


(2) INFORMATION FOR SEQ ID NO:34:

     (i) SEQUENCE CHARACTERISTICS:
          (A) LENGTH: 100 base pairs
          (B) TYPE: nucleic acid
          (C) STRANDEDNESS: single
          (D) TOPOLOGY: linear

   (vii) IMMEDIATE SOURCE:
          (B) CLONE: Frag N7, forward strand

    (xi) SEQUENCE DESCRIPTION: SEQ ID NO:34:

TCGAGAAGAG ATGTGACTTG CCAGAGACCC ACTCCCTTGA CAACAGAAGA ACTTTGATGC     60

TTCTAGACAG AATGAACAGA TTGTCCCCAC ACTCTTGTCT                        100


(2) INFORMATION FOR SEQ ID NO:35:

     (i) SEQUENCE CHARACTERISTICS:
          (A) LENGTH: 116 base pairs
          (B) TYPE: nucleic acid
          (C) STRANDEDNESS: single
          (D) TOPOLOGY: linear

   (vii) IMMEDIATE SOURCE:
          (B) CLONE: Frag N7, reverse strand

    (xi) SEQUENCE DESCRIPTION: SEQ ID NO:35:

CGAAGTCGTG TCTGTCCATA AGACAAGAGT GTGGGGACAA TCTGTTCATT CTGTCTAGAA     60

GCATCAAAGT TCTTCTGTTG TCAAGGGAGT GGGTCTCTGG CAAGTCACAT CTCTTC        116
```

LOW-TOXICITY HUMAN INTERFERON-ALPHA ANALOGS

This application is a continuation-in-part of patent application Serial No. 08/631,328 filed Apr. 12, 1996, now U.S. Pat. No. 5,939,286, herein incorporated by reference.

This invention was made with government support under National Institutes of Health Grant CA69959. Accordingly, the United States government has certain rights in this invention.

FIELD OF THE INVENTION

The present invention relates to a method of reducing the toxicity of human interferon-alpha, to low-toxicity human interferon-alpha analogs, and to the therapeutic uses of these analogs.

REFERENCES

Ausubel, F. M., et al., in CURRENT PROTOCOLS IN MOLECULAR BIOLOGY, John Wiley & Sons, Inc., Media, Pa. (1988).

Benoit, P., et al., *J. Immunol.* 150(3):707 (1993).

Bonnem, E. M., et al., *J. Bio. Response Modifiers* 3:580 (1984).

Davis, G. L., et al., *N. England J. Med.* 321:1501 (1989).

DeMaeyer, E. , et al. , INTERFERONS AND OTHER REGULATORY CYTOKINES, John Wiley and Sons, New York (1988).

Dianzani, F., *J. Interferon Res., Special issue,* 5/92:109 (1992).

Dusheiko, G. M., et al., *J. Hematology* 3(Supl. 2):S199 (1986).

Eaton, M. A. W., et al., U.S. Pat. No. 4,719,180, issued Jan. 12, 1988.

Finter, N. B., et al., *Drugs* 42(5):749 (1991).

Francis, M. L., et al., *AIDS Res. and Human Retro-viruses* 8(2):199 (1992).

Kashima, H., et al., *Laryngoscope* 98:334 (1988).

Maniatis, T., et al., in MOLECULAR CLONING: A LABORATORY MANUAL, Cold Spring Harbor Laboratory (1982).

Martin, E. W., In: DISPENSING OF MEDICATION: A PRACTICAL MANUAL ON THE FORMULATION AND DISPENSING OF PHARMACEUTICAL PRODUCTS (Hoover, J. E., Ed.), 8th edition, Mack Publishing Co., Easton, Pa., (1976).

Oldham, R. K., *Hospital Practice* 20:71 (1985).

Pearson, W. R. and Lipman, D. J., *PNAS* 85:2444–2448 (1988).

Pearson, W. R., *Methods in Enzymology* 183:63–98 (1990).

Pontzer, C. H., et al., *Cancer Res.* 51:5304 (1991).

Quesada, J. R., et al., *N. England J. Med.* 310:15 (1984).

Yoshio, T., et al., U.S. Pat. No. 4,849,350, issued Jul. 18, 1989.

Zoon, K. C., et al., *Methods Enzymol.* 119:312–315 (1986).

BACKGROUND OF THE INVENTION

The interferons (IFNs) have been classified into two distinct groups: type I interferons, including IFNα, IFNβ, IFNτ, and IFNω (also known as IFNαII); and type II interferons, represented by IFNγ (reviewed by DeMaeyer, et al., 1988). In humans, it is estimated that there are at least 17 IFNα non-allelic genes, at least 2 IFNβ non-allelic genes, and a single IFNγ gene.

IFNα's have been shown to inhibit various types of cellular proliferation. IFNα's are especially useful against hematologic malignancies such as hairy-cell leukemia (Quesada, et al., 1984). Further, these proteins have also shown activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, et al., 1984; Oldham, 1985). The role of interferons and interferon receptors in the pathogenesis of certain autoimmune and inflammatory diseases has also been investigated (Benoit, et al., 1993).

IFNα's are also useful against various types of viral infections (Finter, et al., 1991). Alpha interferons have shown activity against human papillomavirus infection, Hepatitis B, and Hepatitis C infections (Finter, et al., 1991; Kashima, et al., 1988; Dusheiko, et al., 1986; Davis, et al., 1989).

Significantly, however, the usefulness of IFNα's has been limited by their toxicity: use of interferons in the treatment of cancer and viral disease results in serious side effects, such as fever, chills, anorexia, weight loss, and fatigue (Pontzer, et al., 1991; Oldham, 1985). These side effects often require (i) the interferon dosage to be reduced to levels that limit the effectiveness of treatment, or (ii) the removal of the patient from treatment. Such toxicity has reduced the usefulness of these potent antiviral and antiproliferative proteins in the treatment of debilitating human and animal diseases.

SUMMARY OF THE INVENTION

In one aspect, the invention includes methods for reducing the toxicity of human IFNα (HuIFNα). The method comprises substituting one or more of the amino acids at positions 19, 20, 22, 24, and 27 of mature HuIFNα with an amino acid effective to substantially reduce the specific toxicity of the polypeptide when exposed to human mononuclear cells in culture. The majority of the amino acid residues 1–27 in mature HuIFNα remains unchanged.

In one embodiment, the method includes substituting nonconserved amino acids for one or more of the amino acids at positions 19, 20, 22, and 27. In various embodiments, the substituting may include, but is not limited to: substituting a class III amino acid, in particular Asp, for the amino acid at position 19; substituting a class IV amino acid, in particular Arg, for the amino acid at position 20; substituting a class III amino acid, in particular Asn, for the amino acid at position 22; and substituting a class IV amino acid, in particular His, for the amino acid at position 27. In another embodiment, the substituting may include substituting a class V amino acid, in particular Leu, for the amino acid at position 24.

In another embodiment, the method comprises substituting the sequence of mature HuIFNα between residues 19–27, with a 9-mer defined by SEQ ID NO:2. In particular, the sequence of mature HuIFNα between residues 19–27 is SEQ ID NO:1. The 9-mer SEQ ID NO:2 corresponds to residues 19–27 of mature ovine interferon-tau (OvIFNτ) and contains residues non-identical to mature HuIFNα at positions 19, 20, 22, 24, and 27. In another embodiment, the method comprises substituting the sequence of HuIFNα between residues 11–27 with a 17-mer defined by SEQ ID NO:4. In particular, the sequence of mature HuIFNα between residues 11–27 is SEQ ID NO:3. The 17-mer SEQ ID NO:4 corresponds to residues 11–27 of mature OvIFNτ, and contains residues non-identical to HuIFNα at positions 11, 13, 14, 16, 19, 20, 22, 24, and 27. In another embodiment, the method comprises substituting the sequence of HuIFNα between residues 6–27 with a 22-mer defined by SEQ ID NO:6. In particular, the sequence of mature HuIFNα between residues 6–27 is SEQ ID NO:5. The 22-mer SEQ ID NO:6 corresponds to residues 6–27 of mature OvIFNτ, and contains residues non-identical to HuIFNα at positions 6, 7, 8, 11, 13, 14, 16, 19, 20, 22, 24, and 27.

In a related aspect, the invention includes a method for reducing the toxicity of HuIFNα. The method includes substituting, for one or more of the amino acids at positions 19, 20, 22, 24, and 27 of mature HuIFNα, an amino acid effective to substantially reduce the specific toxicity of the polypeptide in mononuclear cells in culture, where the mature HuIFNα sequence between residues 28–166 is substantially unchanged. In one embodiment, said substituting is accomplished by substituting the sequence of HuIFNα between residues 1–27 with the 27-mer defined by SEQ ID NO:8. In particular, the sequence of mature HuIFNα between residues 1–27 is SEQ ID NO:7. The 27-mer SEQ ID NO:8 corresponds to residues 1–27 of mature OvIFNτ, and contains residues non-identical to mature HuIFNα at positions 2, 4, 5, 6, 7, 8, 11, 13, 14, 16, 19, 20, 22, 24, and 27.

In another aspect, the invention includes a low-toxicity human IFNα analog for use in human therapy. This analog comprises a mature HuIFNα protein having, at one or more of the amino acid positions 19, 20, 22, 24, and 27, a substituted amino acid, and the majority of the amino acid residues 1–27 in the analog are native HuIFNα residues. The analog is characterized as having a substantially reduced specific toxicity relative to native human IFNα, as evidenced by an increased viability of mononuclear cells in culture.

In one embodiment, the analog contains a nonconserved amino acid substitution at one or more of the positions 19, 20, 22, and 27. In various embodiments, the substituted amino acid may include, but is not limited to: a class III amino acid, in particular Asp, for the amino acid at position 19; a class IV amino acid, in particular Arg, for the amino acid at position 20; a class III amino acid, in particular Asn, for the amino acid at position 22; and a class IV amino acid, in particular His, for the amino acid at position 27. In another embodiment, the substituted amino acid may include a class V amino acid, in particular Leu, for the amino acid at position 24.

In another embodiment, the analog comprises mature human IFNα substituted between residues 19–27 with the 9-mer of SEQ ID NO:2. In another embodiment, the analog comprises mature human IFNα substituted between residues 11–27 with the 17-mer of SEQ ID NO:4. In another embodiment, the analog comprises mature human IFNα substituted between residues 6–27 with the 22-mer of SEQ ID NO:6.

In a related aspect, the invention includes a low-toxicity human IFNα analog for use in human therapy, comprising a mature human IFNα protein having, at one or more of the amino acid positions 19, 20, 22, 24, and 27, a substituted amino acid, with the mature human IFNα sequence between residues 28–166 being substantially unchanged. The analog is characterized by a substantially reduced specific toxicity relative to native mature human IFNα as evidenced by an increased viability of mononuclear cells in culture. In one embodiment, the analog comprises mature human IFNα substituted between residues 1–27 with the 27-mer of SEQ ID NO:8.

The invention further includes a method of inhibiting tumor cell growth. In the method, the tumor cells are contacted with a low-toxicity IFNα analog of the type described above at a concentration effective to inhibit growth of the tumor cells. The low-toxicity IFNα analog may be a part of any acceptable pharmacological formulation. Tumor cells whose growth may be inhibited by a low-toxicity IFNα analog include, but are not limited to, carcinoma cells, hematopoietic cancer cells, leukemia cells, lymphoma cells, and melanoma cells. In one embodiment, the tumor cells are steroid-sensitive tumor cells, for example, mammary tumor cells.

In yet another aspect of the present invention, a low-toxicity IFNα analog of the type described above is used in a method of inhibiting viral replication. In this method, cells infected with a virus are contacted with the low-toxicity IFNα compound at a concentration effective to inhibit viral replication within said cells. The low-toxicity IFNα may be a part of any acceptable pharmacological formulation. The replication of both RNA and DNA viruses may be inhibited by low-toxicity human IFNα. Exemplary RNA viruses include feline leukemia virus, ovine progressive pneumonia virus, ovine lentivirus, equine infectious anemia virus, bovine immunodeficiency virus, visna-maedi virus, caprine arthritis encephalitis virus, human immunodeficiency virus (HIV) or hepatitis c virus (HCV). An exemplary DNA virus is hepatitis B virus (HBV).

In still another aspect, the present invention includes a method of treating an autoimmune disease in a subject in need of such treatment. In one embodiment, the autoimmune disease is multiple sclerosis. The method includes administering, to the subject, a pharmaceutically effective amount of a low-toxicity human IFNα analog of the type described above.

In another aspect, the present invention includes a method of treating chronic inflammation in a subject in need of such treatment. In one embodiment, the chronic inflammation arises from ulcerative colitis. The method includes administering, to the subject, a pharmaceutically effective amount of a low-toxicity human IFNα analog of the type described above.

In yet another aspect, the invention includes a method of treating any disease condition which is responsive to intravenously-administered IFNα, by orally administering a low-toxicity human IFNα analog of the type described above. Orally-administered analog is preferably ingested by the subject.

These and other objects and features of the invention will be more fully appreciated when the following detailed description of the invention is read in conjunction with the accompanying drawings.

BRIEF DESCRIPTION OF THE FIGURES

FIG. 1 shows the alignment of the first 27 N-terminal amino acids of mature HuIFNα, mature OvIFNτ, and eight HuIFNα analogs designated IFNα-N0 through IFNα-N7.

BRIEF DESCRIPTION OF THE SEQUENCES

SEQ ID NO:1 is the amino acid sequence of human IFNα (HuIFNα) between residues 19–27.

SEQ ID NO:2 is the amino acid sequence of ovine interferon-tau (OvIFNτ) between residues 19–27.

SEQ ID NO:3 is the amino acid sequence of HuIFNα between residues 11–27.

SEQ ID NO:4 is the amino acid sequence of OvIFNτ between residues 11–27.

SEQ ID NO:5 is the amino acid sequence of HuIFNα between residues 6–27.

SEQ ID NO:6 is the amino acid sequence of OvIFNτ between residues 6–27.

SEQ ID NO:7 is the amino acid sequence of HuIFNα between residues 1–27.

SEQ ID NO:8 is the amino acid sequence of OvIFNτ between residues 1–27.

SEQ ID NO:9 is the amino acid sequence of mature HuIFNα (IFNα-d; GenBank Accession No. J00210, PID g386796).

SEQ ID NO:10 is the amino acid sequence of the IFNα analog IFNα-N0.

SEQ ID NO:11 is the amino acid sequence of the IFNα analog IFNα-N1.

SEQ ID NO:12 is the amino acid sequence of the IFNα analog IFNα-N2.

SEQ ID NO:13 is the amino acid sequence of the IFNα analog IFNα-N3.

SEQ ID NO:14 is the amino acid sequence of the IFNα analog IFNα-N4.

SEQ ID NO:15 is the amino acid sequence of the IFNα analog IFNα-N5.

SEQ ID NO:16 is the amino acid sequence of the IFNα analog IFNα-N6.

SEQ ID NO:17 is the amino acid sequence of the IFNα analog IFNα-N7.

SEQ ID NO:18 is the amino acid sequence of mature OvIFNτ (oTP-1; GenBank Accession No. Y00287; PID g1358).

SEQ ID NO:19 is the nucleotide sequence for the synthetic gene encoding the analog IFNα-N0.

SEQ ID NO:20 is the nucleotide sequence for Linker1.

SEQ ID NO:21 is the nucleotide sequence for Linker2.

SEQ ID NO:22 is the nucleotide sequence for Fragment N1, forward strand.

SEQ ID NO:23 is the nucleotide sequence for Fragment N1, reverse strand.

SEQ ID NO:24 is the nucleotide sequence for Fragment N2, forward strand.

SEQ ID NO:25 is the nucleotide sequence for Fragment N2, reverse strand.

SEQ ID NO:26 is the nucleotide sequence for Fragment N3, forward strand.

SEQ ID NO:27 is the nucleotide sequence for Fragment N3, reverse strand.

SEQ ID NO:28 is the nucleotide sequence for Fragment N4, forward strand.

SEQ ID NO:29 is the nucleotide sequence for Fragment N4, reverse strand.

SEQ ID NO:30 is the nucleotide sequence for Fragment N5, forward strand.

SEQ ID NO:31 is the nucleotide sequence for Fragment N5, reverse strand.

SEQ ID NO:32 is the nucleotide sequence for Fragment N6, forward strand.

SEQ ID NO:33 is the nucleotide sequence for Fragment N6, reverse strand.

SEQ ID NO:34 is the nucleotide sequence for Fragment N7, forward strand.

SEQ ID NO:35 is the nucleotide sequence for Fragment N7, reverse strand.

DETAILED DESCRIPTION OF THE INVENTION

I. Definitions

Interferon-alpha (IFNα) refers to any one of a family of interferon proteins having greater than 70%, or preferably greater than about 80%, or more preferably greater than about 90% amino acid homology to the mature IFNα protein sequence presented as SEQ ID NO:9. Amino acid homology can be determined using, for example, the LALIGN program with default parameters. This program is found in the FASTA version 1.7 suite of sequence comparison programs (Pearson and Lipman 1988; Pearson, 1990; program available from William R. Pearson, Department of Biological Chemistry, Box 440, Jordan Hall, Charlottesville, Va.). Typically, IFNα has at least one characteristic from the following group of characteristics: (a) anti-viral properties, (b) anti-cellular proliferation properties, and (c) inducible by nucleic acids or by viruses. Preferred IFNα's are from human.

Interferon-tau (IFNτ) refers to any one of a family of interferon proteins having greater than 70%, or preferably greater than about 80%, or more preferably greater than about 90% amino acid homology to the mature IFNτ sequence presented as SEQ ID NO:18. Typically, IFNτ has at least one characteristic from the following group of characteristics: (a) expressed during embryonic/fetal stages by trophectoderm/placenta, (b) anti-luteolytic properties, (c) anti-viral properties, and (d) anti-cellular proliferation properties. Preferred IFNτ's are ovine and bovine IFNτ.

"Mature protein" refers to the IFN protein after removal of the leader sequence. The mature IFN protein sequence begins with residue Cys 24 of the complete IFN amino acid sequence, which corresponds to Cys 1 of the mature protein sequence.

A polynucleotide sequence or fragment is "derived from" another polynucleotide sequence or fragment when it contains the same sequence of nucleotides as are present in the sequence or fragment from which it is derived. For example, a bacterial plasmid contains an insert "derived from" a selected human gene if the sequence of the polynucleotides in the insert is the same as the sequence of the polynucleotides in the selected human gene.

Similarly, a polypeptide sequence or fragment is "derived from" another polypeptide sequence or fragment when it contains the same sequence of amino acids as are present in the sequence or fragment from which it is derived.

Percent (%) identity, with respect to two amino acid sequences, refers to the % of residues that are identical in the two sequences when the sequences are optimally aligned and no penalty is assigned to "gaps". In other words, if a gap needs to be inserted into a first sequence to optimally align it with a second sequence, the % identity is calculated using only the residues that are paired with a corresponding amino acid residue (i.e., the calculation does not consider residues in the second sequences that are in the "gap" of the first sequence). Optimal alignment is defined as the alignment giving the highest % identity score. Such alignments can be preformed using the "GENEWORKS" program. Alternatively, alignments may be performed using the local alignment program LALIGN with a ktup of 1, default parameters and the default PAM.

A "conservative substitution" refers to the substitution of an amino acid in one class by an amino acid in the same class, where a class is defined by common physiochemical amino acid sidechain properties and high substitution frequencies in homologous proteins found in nature (as determined by a standard Dayhoff frequency exchange matrix).

Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

A "non-conservative substitution" refers to the substitution of an amino acid in one class with an amino acid from another class; for example, substitution of an Ala, a class II residue, with a class III residue such as Asp, Asn, Glu, or Gln.

Treating a disease refers to administering a therapeutic substance effective to reduce the symptoms of the disease and/or lessen the severity of the disease.

II. Low-toxicity Human IFNα Analogs

The present invention is based on the discovery that the cytotoxicity of HuIFNα can be significantly reduced by introducing amino acid substitutions at one or more of amino acids positions 19, 20, 22, 24, and 27 in mature HuIFNα.

FIG. 1 shows the first 27 N-terminal amino acid residues of mature HuIFNα (SEQ ID NO:9) and mature OvIFNτ (SEQ ID NO:18) where the non-identical residues are shown in bold. HuIFNα analogs containing subsets of the OvIFNτ substitutions were prepared as described in Example 1. Positions 1–27 of each HuIFNα analog are shown in FIG. 1 with the substitutions shown in bold. Amino acids 28–166 of each analog remain HuIFNα residues (e.g., residues 28–166 of SEQ ID NO:9).

The HuIFNα analogs, designated IFNα-N0 through IFNα-N7 (SEQ ID NO:10 through SEQ ID NO:17), were assayed for cytotoxicity as described in Examples 2 and 3. Hepatocytes incubated with HuIFNα showed significant decreases in viability (Table 1, Example 2). In contrast, cells incubated with the IFNα analog IFNα-N0 showed essentially no loss of viability, as reported in the parent application.

Analogs IFNα-N1 through IFNα-N7 were assayed for cytotoxicity as described in Example 3. Peripheral blood mononuclear cells (PBMCs) incubated with varying amounts of OvIFNτ or the analog IFNα-N0 showed essentially no loss of viability after seven days of incubation. PBMCs incubated with the analogs -N1 or -N3 showed significant decreases in viability, with levels similar to that observed for HuIFNα. Substitutions in analogs -N1 and -N3, at positions 2, 4, 5, 6, 7, 8, 11, 13, and 14, are therefore relatively ineffective in reducing the cytotoxicity of HuIFNα. Cells incubated with IFNα-N4 retained a level of viability between that of cells incubated with HuIFNα and with OvIFNτ. The additional substitutions at positions 16, 19, and 20 are therefore partially effective in reducing the toxicity of HuIFNα.

PBMCs incubated with IFNα analogs IFNα-N5, IFNα-N6, and IFNα-N7 showed essentially no loss of viability after seven days of incubation (Table 2). These 3 analogs retain the low cytotoxicity of OvIFNτ and further define the positions responsible for reduced cytotoxicity of HuIFNα. Most strikingly, the analog IFNα-N7 contains only five substitutions, at positions 19, 20, 22, 24, and 27. The other analogs which exhibit low cytotoxicity, -NO, -N5, and -N6, contain substitutions in these positions and in additional positions (FIG. 1). The analog IFNα-4, which shows an intermediate level of cytotoxity in this test, lacks the substitutions at positions 22, 24, and 27. The data demonstrate that residue positions 19, 20, 22, 24, and 27, play a significant role in the cytotoxicity of these proteins, in accordance with the invention.

More specifically, the present invention contemplates a HuIFNα analog containing one or more amino acid substitutions at positions 19, 20, 22, 24 and 27, with the majority-of the remaining amino acids native HuIFNα residues. The analog possesses reduced toxicity as measured by the cytotoxicity assays described herein, along with therapeutic properties associated with native human IFNα.

Preferred substitutions include one or more of the following: amino acid 19 of mature HuIFNα may be substituted with Asp 19 of mature OvIFNτ, or with a same-class residue Asn, Gln, or Glu; amino acid 20 of mature HuIFNα may be substituted with Arg 20 of mature OvIFNτ or with a same-class residue His or Lys; amino acid 22 of mature HuIFNα may be substituted with Asn 22 of mature OvIFNτ or with a same-class residue Asp, Gln, or Glu; amino acid 24 of mature HuIFNα may be substituted with Leu 24 of mature OvIFNτ or with a same-class residue Val or Met; and amino acid 27 of mature HuIFNα may be substituted with His 27 of OvIFNτ or with a same-class residue Arg or Lys. Such substitutions are effective to reduce the toxicity of HuIFNα but not significantly alter desirable HuIFNα therapeutic properties.

Other exemplary sequences which encompass the altered positions of some low-toxicity HuIFNα analogs include the sequences presented herein as SEQ ID NO:2, SEQ ID NO:4, and SEQ ID NO:6. Most preferred embodiments are HuIFNα analogs substituted in the 19–27 region in positions which are non-identical in OvIFNτ. For example, constructs where amino acids 19–27 of mature human IFNα (SEQ ID NO:1) are substituted for amino acids 19–27 of mature OvIFNτ (SEQ ID NO:2), result in the alteration of positions 19, 20, 22, 24, and 27 in mature human IFNα, while the remaining mature human IFNα sequence remains unchanged. This example corresponds to the analog IFNα-N7 (SEQ ID NO:17).

It will be appreciated that although the low-toxicity human IFNα analogs described are "mature" proteins, that is, they begin with residue Cys 24 of the complete interferon sequence (which corresponds to Cys 1 of the mature protein), the invention also includes IFNα analogs which contain the leader sequence, i.e., that begin with the initiation methionine. The leader sequence in such human IFNα analogs may be derived from human IFNα, ovine IFNτ, or another type I interferon.

As pointed out above, a considerable advantage contemplated for HuIFNα analogs of the present invention is reduced toxicity of the analogs relative to native human IFNα. The HuIFNα analogs may have the same biological activity as the native human IFNα.

III. Recombinant and Synthetic Manipulations

The construction of a synthetic gene encoding HuIFNα analog IFNα-N0 is described in Example 1A. Briefly, amino acid sequence of mature HuIFNα containing all 15 OvIFNτ substitutions within the first 27 N-terminal positions (SEQ ID NO:10) was back translated with codon usage optimized for *Pichia pastoris*. The nucleotide sequence was edited to include five restriction sites spaced throughout the length of the construct. The synthetic gene sequence was divided into four nucleotide fragments. The individual fragments, each approximately 150 base pairs in length, were constructed by sequential ligations of oligonucleotides. The fragments were sequentially cloned into a bacterial vector to yield the gene encoding IFNα-N0 (SEQ ID NO:19). The synthetic gene was then cloned into the pPICZ-α vector for expression in *Pichia pastoris*. The synthetic genes encoding analogs IFNα-N1 through IFNα-N7 were also constructed by sequential ligations of oligonucleotides as described in Example 1A.

Expression of the synthetic genes in Pichia (Example 1B) allowed overproduction of recombinant HuIFNα analogs. The recombinant HuIFNα analogs exhibited antiviral activity (Example 1C) similar to the antiviral activity of recombinant OvIFNτ expressed using the same *Pichia pastoris* system.

IV. Utility

A. Antiviral Properties

Type I interferons exhibit potent antiviral properties. The reduced toxicity of IFNτ with respect to IFNα appears to be attributable to non-conserved amino acids present within the first 27 N-terminal residues of the mature protein. Substitution of these amino acid residues for the corresponding residues in the N-terminal portion of IFNα appears to confer reduced cytotoxicity to the resulting HuIFNα analogs while the antiviral activity of Type I interferons is retained. Thus, formulations comprising low-toxicity HuIFNα analogs of the present invention may be used to inhibit viral replication.

The low-toxicity HuIFNα analogs of the present invention can be employed in methods for affecting the immune relationship between fetus and mother, for example, in preventing transmission of maternal viruses (e.g., HIV) to the developing fetus. The human interferon analogs are particularly useful for treatment of humans, since potential antigenic responses are less likely using a homologous protein.

B. Anticellular Proliferation Properties

Type I interferons exhibit potent anticellular proliferation activity. Low-toxicity human IFNα analogs such as described herein can also be used to inhibit cellular growth without the negative side effects associated with other interferons which are currently known. Formulations comprising the low-toxicity IFNα analogs of the present invention can be used to inhibit, prevent, or slow tumor growth.

C. Immune System Disorders

Diseases which may be treated using methods of the present invention include autoimmune, inflammatory, proliferative and hyperproliferative diseases, as well as cutaneous manifestations of immunologically mediated diseases. In particular, methods of the present invention are advantageous for treating conditions relating to immune system hypersensitivity. There are four types of immune system hypersensitivity. Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

The mechanisms by which certain conditions may result in hypersensitivity in some individuals are generally not well understood, but may involve both genetic and extrinsic factors. For example, bacteria, viruses or drugs may play a role in triggering an autoimmune response in an individual who already has a genetic predisposition to the autoimmune disorder. It has been suggested that the incidence of some types of hypersensitivity may be correlated with others. For example, it has been proposed that individuals with certain common allergies are more susceptible to autoimmune disorders.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barré Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Crohn's disease and ulcerative colitis, as well as food-related allergies.

Autoimmune diseases particularly amenable for treatment using the methods of the present invention include multiple sclerosis, type I (insulin dependent) diabetes mellitus, lupus erythematosus, amyotrophic lateral sclerosis, Crohn's disease, rheumatoid arthritis, stomatitis, asthma, uveitis, allergies and psoriasis.

Medicaments containing low-toxicity HuIFNα analogs of the present invention may be used to therapeutically treat and thereby alleviate symptoms of autoimmune disorders such as those discussed above.

D. Pharmaceutical Compositions

Low-toxicity human IFNα analogs of the present invention can be formulated according to known methods for preparing pharmaceutically useful compositions. Formulations comprising interferons or interferon-like compounds have been previously described (for example, Martin, 1976). In general, the compositions of the subject invention will be formulated such that an effective amount of the interferon analog is combined with a suitable carrier in order to facilitate effective administration of the composition.

The compositions used in these therapies may also be in a variety of forms. These include, for example, solid, semi-solid, and liquid dosage forms, such as tablets, pills, powders, liquid solutions or suspensions, liposomes, suppositories, injectable, and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

Low-toxicity human IFNα analogs or related polypeptides may be administered to a patient in any pharmaceutically acceptable dosage form, including oral intake, inhalation, intranasal spray, intraperitoneal, intravenous, intramuscular, intralesional, or subcutaneous injection. Specifically, compositions and methods used for other interferon compounds can be used for the delivery of these analogs.

One primary advantage of the IFNα analogs of the subject invention, however, is their extremely low cytotoxicity. Because of this low toxicity, it is possible to administer the interferon analogs in concentrations which are greater than those which can generally be utilized for other interferon (e.g., native human IFNα) compounds. Thus, it is contemplated that low-toxicity HuIFNα analogs of the present invention can be administered at rates from about $5\times10^4$ to $20\times10^6$ units/day to about $500\times10^6$ units/day or more. In a preferred embodiment, the dosage is about $20\times10^6$ units/day. High doses are preferred for systemic administration. It should, of course, be understood that the compositions and methods of this invention may be used in combination with other therapies.

Once improvement of a patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

The IFNα analogs of the subject invention can be administered through standard procedures to treat a variety of cancers and viral diseases including those for which other interferons have previously shown activity. See, for example, Finter, et al., 1991; Dianzani, 1992; Francis, et al., 1992, and U.S. Pat. Nos. 4,885,166 and 4,975,276. However, as discussed above, the IFNα analogs of the subject invention have unique features and advantages, including their ability to treat these conditions without toxicity.

E. Treatment of Skin Disorders

Disorders of the skin can be treated intralesionally using low-toxicity interferon analogs of the present invention, wherein formulation and dose will depend on the method of administration and on the size and severity of the lesion to be treated. Preferred methods include intradermal and subcutaneous injection. Multiple injections into large lesions may be possible, and several lesions on the skin of a single patient may be treated at one time. The schedule for administration can be determined by a person skilled in the art. Formulations designed for sustained release can reduce the frequency of administration.

F. Systemic Treatment

Systemic treatment is essentially equivalent for all applications. Multiple intravenous, subcutaneous and/or intramuscular doses are possible, and in the case of implantable methods for treatment, formulations designed for sustained release are particularly useful. Patients may also be treated using implantable subcutaneous portals, reservoirs, or pumps.

G. Regional Treatment

Regional treatment with the low-toxicity IFNα analogs of the present invention is useful for treatment of cancers in specific organs. Treatment can be accomplished by intraarterial infusion. A catheter can be surgically or angiographically implanted to direct treatment to the affected organ. A subcutaneous portal, connected to the catheter, can be used for chronic treatment, or an implantable, refillable pump may also be employed.

The following examples illustrate, but in no way are intended to limit the present invention.

MATERIALS AND METHODS

Restriction endonucleases, T4 DNA ligase, T4 polynucleotide kinase, Taq DNA polymerase, and calf intestinal phosphatase were purchased from New England Biolabs (Beverly, Mass.) or Promega Biotech (Madison, Wis.): these reagents were used according to the manufacturer's instructions. For sequencing reactions, a "SEQUENASE DNA II" sequencing kit was used (United States Biochemical Corporation, Cleveland Ohio). Immunoblotting and other reagents were from Sigma Chemical Co. (St. Louis, Mo.) or Fisher Scientific (Needham, Mass.). Nitrocellulose filters are obtained from Schleicher and Schuell (Keene, N.H.).

Synthetic oligonucleotide linkers and primers were prepared using commercially available automated oligonucleotide synthesizers (e.g., an ABI model 380B-02 DNA synthesizer (Applied Biosystems, Foster City, Calif.)). Alternatively, custom designed synthetic oligonucleotides may be purchased, for example, from Synthetic Genetics (San Diego, Calif.). CDNA synthesis kit and random priming labeling kits were obtained from Boehringer-Mannheim Biochemical (BMB, Indianapolis, Ind.).

Oligonucleotide sequences encoding polypeptides can be either synthesized directly by standard methods of oligonucleotide synthesis, or, in the case of large coding sequences, synthesized by a series of cloning steps involving a tandem array of multiple oligonucleotide fragments corresponding to the coding sequence (Yoshio, et al., 1989; Eaton, et al., 1988). Oligonucleotide coding sequences can be expressed by standard recombinant procedures (Maniatis, et al., 1982; Ausubel et al., 1988). Alternatively, peptides can be synthesized directly by standard in vitro techniques (Applied Biosystems, Foster City Calif.).

Recombinant Human IFNαA was obtained from Biosource International (Camarillo, Calif.). Unless otherwise indicated, protein concentration was determined with the bicinchoninic acid assay kit (Pierce, Rockford Ill.) according to the manufacturer's instructions.

All tissue culture media, sera and IFNs used in this study were negative for endotoxin, as determined by assay with Limulus amebocyte lysate (Associates of Cape Cod, Woods Hole, Mass.) at a sensitivity level of 0.07 ng/ml.

EXAMPLE 1

Cloning and Expression of HuIFNα Analogs

A. Construction of Synthetic Genes Encoding HuIFNα Analogs

The amino acid sequence of HuIFNα containing all 15 OvIFNτ substitutions within the first 27 N-terminal positions (SEQ ID NO:10) was back translated with codon usage optimized for *Pichia pastoris*. The nucleotide sequence was edited to include five restriction sites spaced throughout the length of the construct. The synthetic gene sequence was divided into four nucleotide fragments. The individual fragments, each approximately 150 base pairs in length, were constructed by sequential ligations of oligonucleotides. The fragments were sequentially cloned into the G2 bacterial vector to yield the gene encoding IFNα-N0 (SEQ ID NO:19). The synthetic gene was then cut out of the bacterial vector and ligated into the XhoI/NotI sites of the pPICZ-α vector (Invitrogen, San Diego Calif.) for expression in *Pichia pastoris*.

The synthetic genes encoding analogs IFNα-N1 through IFNα-N7 were also constructed by sequential ligations of oligonucleotides. The pPICZ-α/IFNα-N0 construct described above was digested with XbaI and BstEII and annealed oligonucleotides Linker1 (SEQ ID NO:20) and Linker2 (SEQ ID NO:21) were ligated into these sites to produce an intermediate vector construct. This step removed the nucleotide sequence corresponding to the N-terminal section of IFNα-N0, to be replaced by the nucleotide fragments listed below. The intermediate vector construct was digested with XhoI and EcoRI. The following nucleotide fragments, prepared by sequential ligation of oligonucleotides, were then ligated into the XhoI/EcoRI sites of the intermediate construct to produce analogs IFNα-N1 through IFNα-N7 in the pPICZ-α vector.

| | | |
|---|---|---|
| IFNα-N1 | Fragment N1 forward | SEQ ID NO: 22 |
| | Fragment N1 reverse | SEQ ID NO: 23 |
| IFNα-N2 | Fragment N2 forward | SEQ ID NO: 24 |
| | Fragment N2 reverse | SEQ ID NO: 25 |
| IFNα-N3 | Fragment N3 forward | SEQ ID NO: 26 |
| | Fragment N3 reverse | SEQ ID NO: 27 |
| IFNα-N4 | Fragment N4 forward | SEQ ID NO: 28 |
| | Fragment N4 reverse | SEQ ID NO: 29 |
| IFNα-N5 | Fragment N5 forward | SEQ ID NO: 30 |
| | Fragment N5 reverse | SEQ ID NO: 31 |
| IFNα-N6 | Fragment N6 forward | SEQ ID NO: 32 |
| | Fragment N6 reverse | SEQ ID NO: 33 |
| IFNα-N7 | Fragment N7 forward | SEQ ID NO: 34 |
| | Fragment N7 reverse | SEQ ID NO: 35 |

B. Expression of HuIFNα Analogs in Pichia

For expression of the recombinant interferon analogs, the coding sequence of each gene was inserted into the pPICZ-α expression vector (Invitrogen, San Diego, Calif.) using the XhoI and NotI restriction endonuclease sites on the vector. The pPICZ-α expression vector provides a variety of elements to facilitate expression and purification of the recombinant interferons. For example, the vector includes an expression cassette containing the methanol-regulated alcohol oxidase (AOX) promoter. In methanol grown yeast cells, approximately 5% of the polyA+ RNA is from the AOX1 gene. In addition, the vector also contains the secretion signal sequence from the Saccharomyces cerevisiae α factor prepro peptide which directs the secretion of the protein into the culture medium. The vector also provides selection of recombinant bacteria and yeast cells using the Zeocin antibiotic coded for by the Sh ble gene (*Streptoalloteichus hindustanus* ble gene).

The recombinant plasmids encoding HuIFNα analogs were electroporated into the X-33 wild-type *Pichia pastoris* strain for large-scale growth. Recombinant yeast colonies were grown and induced according to the protocols provided by Invitrogen. Supernatants were collected and filtered using a 0.8/0.2 mm pore size acrodisc filter (Gelman Sciences, Ann Arbor, Mich.) and buffer exchanged with phosphate buffered saline (PBS) using Centriplus-10 concentrators (Amicon, Inc., Beverly, Mass.). The recombinant HuIFNα analogs obtained by this method exhibited antiviral activity similar to the antiviral activity of recombinant OvIFNτ expressed using the same *Pichia pastoris* system.

C. Quantitative Antiviral Assay

A calorimetric assay was used to quantitate the antiviral activity of the interferon proteins. Madin Darby bovine kidney (MDBK) cells were grown to confluency in 96-well flat bottom plates using Eagle's MEM supplemented with 10% fetal bovine serum (FBS) and antibiotics. Medium was removed and the cells were washed once with sterile PBS. Samples were added in triplicate using serial 10-fold and 2-fold dilutions at 100 μl/well using Eagle's MEM supplemented with 2% FBS and antibiotics as dilution medium. Interferon samples were added and the cells were incubated for 18 hours at 37° C. Recombinant HuIFN-αA (Biosource Intl.) was used as the standard interferon control. 100 μl of vesicular stomatitis virus (VSV) was added to the test wells and incubated for an additional 48 hours at 37° C. 100 μl of medium was removed from each well and replaced with 100 μl of 0.2% neutral red solution (Gibco-BRL) and incubated for 1 hour at 37° C. All medium was removed and cells were gently washed twice with PBS before addition of 100 μl of acid alcohol (50% ethanol, 1% acetic acid). The $A_{550}$ of solubilized dye was read with a Bio-Kinetics Reader (Bio-Tek Instruments, Winooski Vt.). Percent protection was calculated using the following formula:

$$\text{Percent Protection} = 100 \times \frac{\text{AVG } (A_{550} \text{ Test Well}) - \text{AVG } (A_{550} \text{ Virus Control Well})}{\text{AVG } (A_{550} \text{ Untreated Cell Control Wells}}$$

1 antiviral unit (U) is defined as 50% protection.

EXAMPLE 2

In Vitro Toxicity of IFNα Analogs in Hepatocyes

The in vitro toxicity of HuIFNα and IFNα analog IFNα-N0 (SEQ ID NO:10; FIG. 1) were compared using normal human hepatocytes. Hepatocytes were received as a confluent layer of cells in matrigel-coated 96-well plates from Clonetics Corporation (San Diego, Calif.). The following day, the medium in the wells was replaced with 100 μl of a Modified Williams E Medium (Clonetics Corp.) supplemented with 0.1 μM insulin, 0.1 μM dexamethasone, 50 μg/ml gentamicin, and 50 ng/ml amphotericin B. The cells were subsequently treated with 2000 U/ml to 128,000 U/ml of HuIFNα or IFNα-N0. After 4, 6, or 7 days of incubation, 10 μl of the tetrazolium salt WST-1 (4-3-(4-Iodophenyl)-2-(4-nitrophenyl)-2H-5-tetrazoliol-1-3-benzene disulfonate) (Boehringer Mannheim, Indianapolis Ind.) was added to each well. WST-1 is cleaved to formazan by the succinate-tetrazolium reductase system which is present in the mitochondrial respiratory chain and is active only in viable cells. The percentage of viable cells was measured by absorbance at 450 nm and expressed as the percentage of non-interferon treated cells.

The results are shown in Table 1. Values are presented as percent metabolic activity of viable cells in which 100% is equal to the viability of cells treated with medium alone.

TABLE 1

PERCENT METABOLIC ACTIVITY OF PRIMARY NORMAL HUMAN HEPATOCYTES AFTER 4, 6, OR 7 DAYS INCUBATION WITH IFN SAMPLES

| Days of IFN Treatment | Sample | (UNITS/ML) 1.28 × $10^5$ | 6.4 × $10^4$ | 3.2 × $10^4$ | 1.6 × $10^4$ | 8 × $10^3$ | 4 × $10^3$ | 2 × $10^3$ |
|---|---|---|---|---|---|---|---|---|
| 4 | rHuIFN-α | 70.9 | 74.4 | 92.1 | 72.0 | 71.3 | 77.5 | 91.4 |
| 4 | IFNα-N0 | 114.6 | 130.9 | 142.4 | 122.3 | 112.0 | 93.5 | 111.3 |
| 6 | rHuIFN-α | 58.1 | 68.2 | 96.3 | 112.4 | 76.5 | 73.6 | ND |
| 6 | IFNα-N0 | 118.3 | 96.2 | 114.6 | 129.9 | 138.6 | 110.7 | ND |
| 7 | rHuIFN-α | 35.0 | 47.1 | 71.4 | 66.0 | 82.0 | 83.0 | ND |
| 7 | IFNα-N0 | 94.4 | 132.0 | 139.0 | 97.4 | 111.7 | 155.4 | ND |

ND = not done.

Hepatocytes incubated with HuIFNα showed significant decreases in viability. In contrast, cells incubated with the IFNα analog IFNα-N0 showed essentially no loss of viability in comparison to nontreated cells.

EXAMPLE 3

In Vitro Toxicity of IFNα Analogs in Mononuclear Cells

The in vitro toxicity of HuIFNα, OvIFNτ, and human IFNα analogs IFNα-N0 through IFNα-N7 (SEQ ID NO:10 through SEQ ID NO:17; FIG. 1) were compared using peripheral blood mononuclear cells (PBMC). The buffy coat fraction of whole blood was diluted 1:4 with PBS and overlayed onto Nycoprep 1.077 (Nycomed Pharma, Oslo, Norway). After centrifugation at 600×g for 20 minutes at 20° C., the PBMC which band at the interface were removed using a pipette. The cells were washed once with PBS and plated at a concentration of 2×$10^5$ cells/well in a 96-well plate. The following day the cells were treated with 2000 U/ml to 128,000 U/ml of IFNα, IFNτ, or the IFNα analogs. After seven days of incubation, the tetrazolium salt WST-1 (Boehringer Mannheim), was added to each well. The percentage of viable cells was measured by absorbance at 450 nm and expressed as the percentage of non-interferon treated cells.

The results are shown in Table 2. Values are presented as percent metabolic activity of viable cells in which 100% is equal to the viability of cells treated with medium alone.

TABLE 2

PERCENT METABOLIC ACTIVITY OF HUMAN PERIPHERAL BLOOD MONONUCLEAR CELLS (PBMC) AFTER 7 DAYS INCUBATION WITH IFN SAMPLES

| Sample | (UNITS/ML) 1.28 × $10^5$ | 6.4 × $10^4$ | 3.2 × $10^4$ | 1.6 × $10^4$ | 8 × $10^3$ | 4 × $10^3$ | 2 × $10^3$ |
|---|---|---|---|---|---|---|---|
| rHuIFN-α | 64.4 | 65.0 | 63.8 | 74.1 | 71.6 | 73.6 | 92.5 |
| rOvIFN-τ | 97.4 | 105.7 | 122.5 | 117.5 | 90.2 | 100.9 | 89.7 |
| IFNα-N0 | ND | 124.6 | 138.9 | 101.7 | 103.5 | 103.0 | 105.7 |
| IFNα-N1 | 60.0 | 56.1 | 60.4 | 69.3 | 65.6 | ND | ND |
| IFNα-N3 | 53.8 | 64.1 | 59.0 | 73.5 | 63.7 | 66.6 | 71.7 |
| IFNα-N4 | 82.5 | 80.9 | 80.5 | 76.1 | 89.8 | 71.1 | 73.4 |
| IFNα-N5 | 139.1 | 118.0 | 99.2 | 110.2 | 82.2 | 96.8 | 120.0 |
| IFNα-N6 | ND | 103.4 | 116.5 | 91.4 | 106.9 | 96.0 | 125.3 |
| IFNα-N7 | 97.5 | 150.6 | 96.8 | 121.5 | 159.4 | 111.5 | 140.3 |

ND = Not done.

PBMCs incubated with HuIFNα showed a significant decrease in viability. In contrast, cells incubated with OvIFNτ or with the human IFNα analogs IFNα-N0, IFNα-N5, IFNα-N6, and IFNα-N7 showed essentially no loss of viability after seven days of incubation. Decreases in viability similar to those observed for HuIFNα were observed in cells incubated with IFNα analogs IFNα-N1 and IFNα-N3. Cells incubated with IFNα analog IFNα-N4 showed a small increase in viability over cells incubated with HuIFNα.

While the invention has been described with reference to specific methods and embodiments, it will be appreciated that various modifications and changes may be made without departing from the invention.

It is claimed:

1. A polypeptide analog of a native human interferon (IFN)-α protein, wherein the sequence of amino acids in the analog that corresponds to the sequence of residues 1–27 of the native IFN-α protein differs therefrom at one or more of positions 19, 20, 22, 24, and 27, said sequences differing only at said positions, provided that said sequence in the analog does not differ from said corresponding sequence in the native IFN-α only by the presence of Ser, Thr, Asn, Gln, or Gly at the amino acid residue corresponding to position 22;

and wherein the analog is capable of exhibiting lower toxicity relative to the native IFN-α in an assay comprising:

(a) incubating a first sample of PBMCs for seven days in a culture medium comprising at least 2000 antiviral units/ml of the analog;

(b) incubating a second sample of PBMCs for seven days in a culture medium having an equal concentration, as antiviral units/ml, of the native IFN-α; and (c) comparing the percentage of viable cells remaining in the first sample with that in the second sample, whereby a higher percentage of viable cells indicates the relatively lower toxicity of the IFN species in the culture medium.

2. A polypeptide analog according to claim 1 wherein the amino acid residues corresponding to positions 19, 20, 22, 24, and 27 of the native IFN-α that differ from the corresponding native amino acid residues are related thereto as nonconservative amino acid substitutions.

3. A polypeptide analog according to claim 2 wherein the amino acid residue corresponding to position 19 is Asn, Asp, Gln, or Glu.

4. A polypeptide analog according to claim 2 wherein the amino acid residue corresponding to position 19 is Asp.

5. A polypeptide analog according to claim 2 wherein the amino acid residue corresponding to position 20 is His, Arg, or Lys.

6. A polypeptide analog according to claim 2 wherein the amino acid residue corresponding to position 20 is Arg.

7. A polypeptide analog according to claim 2 wherein the amino acid residue corresponding to position 22 is Asn, Asp, Gln, or Glu.

8. A polypeptide analog according to claim 2 wherein the amino acid residue corresponding to position 22 is Asn.

9. A polypeptide analog according to claim 2 wherein the amino acid residue corresponding to position 27 is His, Arg, or Lys.

10. A polypeptide analog according to claim 2 wherein the amino acid residue corresponding to position 27 is His.

11. A polypeptide analog according to claim 1 wherein the amino acid residue corresponding to position 24 is Ile, Leu, Val, or Met.

12. A polypeptide analog according to claim 1 wherein the amino acid residue corresponding to position 24 is Leu.

13. A polypeptide analog according to claim 1 wherein the sequence of amino acids in the analog that corresponds to the sequence of residues 28–166 of the native IFN-α protein is substantially the same as the latter sequence.

14. A polypeptide analog according to claim 13 wherein the sequence of amino acids in the analog that corresponds to the sequence of residues 28–166 of the native IFN-α protein is the same as the latter sequence.

15. A nucleic acid molecule encoding a polypeptide analog according to claim 1.

16. A nucleic acid molecule encoding a polypeptide analog according to claim 2.

17. A nucleic acid molecule encoding a polypeptide analog according to claim 3.

18. A nucleic acid molecule encoding a polypeptide analog according to claim 4.

19. A nucleic acid molecule encoding a polypeptide analog according to claim 5.

20. A nucleic acid molecule encoding a polypeptide analog according to claim 6.

21. A nucleic acid molecule encoding a polypeptide analog according to claim 7.

22. A nucleic acid molecule encoding a polypeptide analog according to claim 8.

23. A nucleic acid molecule encoding a polypeptide analog according to claim 9.

24. A nucleic acid molecule encoding a polypeptide analog according to claim 10.

25. A nucleic acid molecule encoding a polypeptide analog according to claim 11.

26. A nucleic acid molecule encoding a polypeptide analog according to claim 12.

27. A nucleic acid molecule encoding a polypeptide analog according to claim 13.

28. A nucleic acid molecule encoding a polypeptide analog according to claim 14.

29. A method for making a polypeptide analog of a human IFN-α protein, comprising placing a nucleic acid molecule according to claim 15 in a recombinant expression system;

effecting expression of the nucleic acid so as to produce the analog; and recovering the analog.

30. A method for making a polypeptide analog of a human IFN-α protein, comprising placing a nucleic acid molecule according to claim 27 in a recombinant expression system;

effecting expression of the nucleic acid so as to produce the analog; and recovering the analog.

31. A method for making a polypeptide analog of a human IFN-α protein, comprising placing a nucleic acid molecule according to claim 28 in a recombinant expression system;

effecting expression of the nucleic acid so as to produce the analog; and recovering the analog.

32. A method for making a nucleic acid molecule encoding a polypeptide analog of a human IFN-α protein, comprising modifying a nucleic acid molecule encoding a native human IFN-α protein at one or more codons to afford a nucleic acid molecule according to claim 15.

33. A method for making a nucleic acid molecule encoding a polypeptide analog of a human IFN-α protein, comprising modifying a nucleic acid molecule encoding a native human IFN-α protein at one or more codons to afford a nucleic acid molecule according to claim 27.

34. A method for making a nucleic acid molecule encoding a polypeptide analog of a human IFN-α protein, comprising modifying a nucleic acid molecule encoding a native human IFN-α protein at one or more codons to afford a nucleic acid molecule according to claim 28.

35. A pharmaceutical composition comprising an IFN-α analog according to claim 1 and a pharmaceutically acceptable carrier.

36. A pharmaceutical composition comprising an IFN-α analog according to claim 13 and a pharmaceutically acceptable carrier.

37. A pharmaceutical composition comprising an IFN-α analog according to claim 14 and a pharmaceutically acceptable carrier.

38. A method of inhibiting viral replication in cells infected with a virus, comprising contacting the cells with an IFN-α analog according to claim 1 in an amount effective to inhibit replication of the virus in the cells.

39. A method of inhibiting the growth of tumor cells, comprising contacting the cells with an IFN-α analog according to claim 1 in an amount effective to inhibit their growth.

40. A method of treating an autoimmune disease in a subject, comprising administering to the subject an IFN-α analog according to claim 1 in an amount effective to treat the disease.

41. A method of treating chronic inflammation in a subject, comprising administering to the subject an IFN-α analog according to claim 1 in an amount effective to treat the inflammation.

42. A method of treating a disease condition responsive to IFN-α, comprising administering to a subject having the disease condition an IFN-α analog according to claim 1 by oral administration in an amount effective to treat the disease condition.

* * * * *